United States Patent [19]

Cassou et al.

[11] 4,378,798

[45] Apr. 5, 1983

[54] SINGLE SHOT STOCK OF ANIMAL SEMEN FOR ARTIFICIAL INSEMINATION OF BIRDS, ESPECIALLY TURKEYS, HENS, AND GUINEA FOWL

[76] Inventors: Betrand Cassou, Saint Symphorien les Bruyeres; Maurice Cassou; Robert Cassou, both of Rue Clemenceau, all of 61300 L'Aigle, France

[21] Appl. No.: 276,401

[22] Filed: Jun. 22, 1981

[30] Foreign Application Priority Data

Jan. 8, 1981 [FR] France ............................... 81 00196
May 18, 1981 [FR] France ............................... 81 09864

[51] Int. Cl.³ ............................................. A61M 1/00

[52] U.S. Cl. .................................... 604/275; 604/217; 604/218

[58] Field of Search ............... 128/215, 217, 234, 235, 128/261, 220, 263, 264, 265, 270, 271

[56] References Cited

U.S. PATENT DOCUMENTS 2,183,482 12/1939 Kurkjian ............................. 128/261
2,616,422 11/1952 Jones .................................. 128/261
2,691,980 10/1954 Jones .................................. 128/261
2,709,436 5/1955 Lynn .................................. 128/261
4,173,227 11/1979 Cassou et al. ....................... 128/235

*Primary Examiner*—John D. Yasko
*Attorney, Agent, or Firm*—James C. Wray; Craig B. Bailey

[57] ABSTRACT

The present invention relates to single shot stocks of animal semen to be used for artificial insemination of poultry such as turkeys, hens and guinea fowl, of the kind comprising a tube presenting an opening of relatively small diameter so that the semen introduced therein can be maintained therein by capillarity alone so as to avoid the use of any bung.

The object of the invention is to provide a stock of semen of the kind referred to which avoids any risk of waste of material.

To this end, the invention provides a stock of the kind comprising a tube made of relatively flexible material presenting an opening for receiving the semen whose diameter is significantly greater than the thickness of the cylindrical wall, one end of the tube terminating in a brim forming by bending the end of the wall within the tube, characterized in that this brim is shaped so that its free edge comes into direct contact with main cylindrical wall of the tube.

11 Claims, 3 Drawing Figures

SINGLE SHOT STOCK OF ANIMAL SEMEN FOR ARTIFICIAL INSEMINATION OF BIRDS, ESPECIALLY TURKEYS, HENS, AND GUINEA FOWL

The present invention relates to single shot stocks of animal semen to be used for artificial insemination of poultry such as turkeys, hens and guinea fowl, of the kind comprising a tube presenting an opening of relatively small diameter so that the semen introduced therein can be maintained therein by capillarity alone so as to avoid the use of any bung. The semen is generally introduced therein by pressure and is placed, after introducing one end into the vagina and uterus of the animal, by blowing using a pressure device such as a bulb. The tubes are thrown away after use so as to avoid any contamination, and so they are dimensioned so as to contain only a single dose of semen, nonetheless being sufficient to ensure effective insemination, for example 15 to 50 mm 3 only according to the animal species, and this explains how it can be maintained by capillarity alone. The absence of a bung considerably simplifies handling in the case where the paillette is to be used for insemination immediately after being filled, without being stored in the meantime.

Stocks of this kind are known, called catheters, which have a wall thickness very much thicker than the diameter of the opening, up to twice this diameter even, and which are consequently extremely rigid and thus present the disadvantage of risking injury, in a large number of cases, to the internal mucous of the animal, all the more so since the edge of the front end of such a catheter is generally relatively sharp or cutting, and thus aggressive, even if this end has been ground in. These catheters, in general made out of polystyrene, are too rigid and therefore do not allow any composition for possible rough handling, even accidental, by the user so that this can lead to irritation and even damage to the mucous of the cloaca, which is very serious, as it reduces considerably the fertility of the animal. Moreover, as the internal opening is perfectly straight, at the slightest mechanical shock, during handling in the poultry run, one or more drops of semen fall to the ground or into the hand during filling of these catheters, which cause significant waste of a matter which is relatively precious, particularly in the case of an animal selected for its qualities, which leads to a financial operating deficiency which is significant and unnecessary.

Other stocks of this kind are known, called paillettes, whose wall thickness is much thinner, which leads in addition to a significant reduction in outer diameter (of the order of half of the above catheters) so that these paillettes are much more flexible, can be bent without breaking and, in any case, enable the unfortunate consequences of over-energetic handling by the operator to be softened or eliminated. To this is added the advantage that at the beginning of the laying cycle, the bird's cloaca, which is relatively contracted in young animals, runs less risk of being injured due to the significantly reduced diameter of such a paillette.

However, these known stocks, in order to present a rounded edge which does not cause injury on introduction, have a brim of the same thickness as the wall and formed by bending the wall back within the tube, parallel to the main wall of the tube so as to form a "U" shape in section, this brim or hem extending over an axial length of the order of magnitude of the diameter of the opening.

Nonetheless, these stocks or paillettes, already improved, still present various disadvantages. Thus, in particular, because of the "U" shape section mentioned above, part of the semen contained in the paillette cannot be ejected through the outlet orifice defined by the brim, so that it collects in a ring shape between the end of this brim and the main wall and is thus totally wasted for the insemination operation, leading to a financial deficiency. Moreover, during a mechanical shock, there is still a risk of the semen being expelled out of the tube, and a drop can fall to the ground and lead, again to a waste of material.

Accordingly, the object of the invention is to provide a stock of semen of the kind referred to which avoids any risk of waste of material.

To this end, the invention provides a stock of the kind comprising a tube made of relatively flexible material presenting an opening for receiving the semen whose diameter is significantly greater than the thickness of the cylindrical wall, one end of the tube terminating in a brim formed by bending the end of the wall within the tube, characterised in that this brim is shaped so that its free edge comes into direct contact with main cylindrical wall of the tube.

Due to this arrangement, during deliberate expulsion of the semen for insemination, none of the semen is retained in the paillette thus avoiding any costly waste. In addition, because of the shape analogous to a trumpet or venturi presented by the brim on one hand there is retention of the column of semen in the vicinity of the part of the brim converging towards the outside when no pressure is applied to the other end of the tube, thus during handling, so that one avoids expulsion of semen which a shock would risk producing, and on the other hand, on the contrary, the second diverging part of the brim facilitates total expulsion when pressure is applied for the insemination.

In a particularly advantageous fashion, a member of revolution forming a piston can be provided within the tube in sliding and sealing relation within it.

With this design, the piston member is used both by its backwards movement when the semen is sucked into the paillette-tube, and by its forward movement when the semen is expelled during the insemination itself. The means for displacing the piston during the inspiration and expulsion movements can be mechanical (plunger), hydraulic or pneumatic.

The presence of the piston and the resulting retention of the semen column once it is sucked in, between the piston and the brim or hem gives total retention of the semen inside the tube whatever the mechanical shocks, sometimes violent, which can happen to the tube during the many manipulations occurring between inspiration and expulsion of the semen. It follows from the double safety precautions given by the brim and by the piston, that no waste of semen can occur during handling, which is essential because of the high price of the semen in poultry farming, particularly for stud birds.

Moreover, the piston forms a member permanently interposed between the means or agent of inspiration and expulsion of the semen and the semen itself and due to this fact there is no risk of contamination of the semen. Thus the presence of the piston and its perfect sealing relation with the tube avoids the atmosphere of the poultry run penetrating down the tube during insemination. In addition, the piston enables complete expulsion of the semen, into the bird's cloaca during its forward movement towards the brim and produces a suction phenomenon like a syringe during its backward movement.

In a particularly advantageous embodiment of the invention, where the brim of the tube presents an inner part converging towards the wall of the tube, the end of the piston facing the brim of the tube can have an end shape which mates at least approximately with this inner converging part. In this way, during expulsion of the semen, this end of the piston presses close up to the inner part of the brim, leaving practically no free space, so that the semen is totally expelled without any waste during insemination as well, in addition to the absence of waste during handling as indicated above. Preferably the said end of the piston has a truncated cone shape.

Advantageously, in the case where the means for sucking in the semen and expelling it again comprise a thrust rod, one end of the piston, opposite the brim of the tube, can be provided with a blind hole, in which the thrust rod can be press fitted and control readily the forwards and backwards movements of the piston.

Other features and advantages of the invention will appear from the following description, by way of non-limitative example, with reference to the accompanying drawings, in which.

Figure 1:
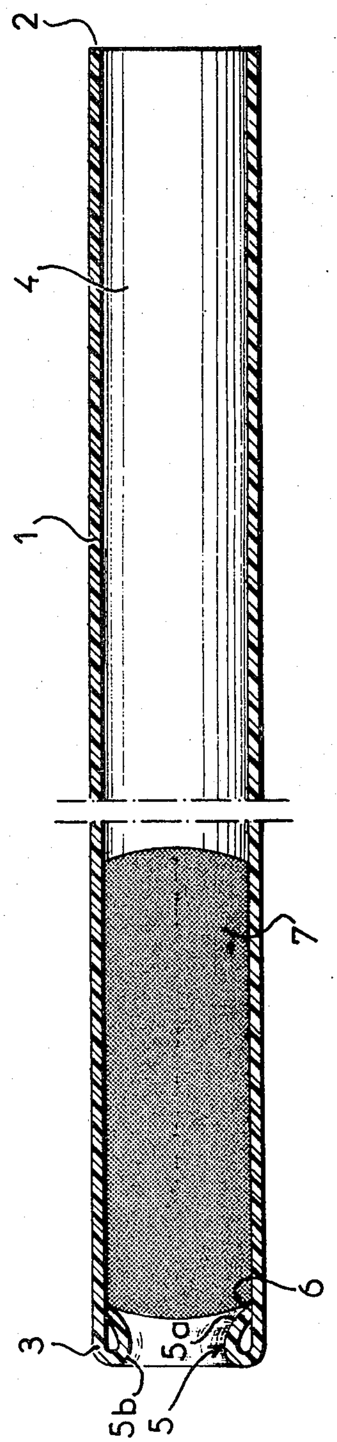
FIG. 1 shows a semen stock, in a first embodiment in accordance with the invention.

The stock shown in FIG. 1 comprises a single part in the shape of a tube 1 which is made out of relatively flexible material such as polyvinyl chloride, this tube being perfectly cylindrical over its whole length between its two ends 2 and 3, the main cylindrical wall of this tube having a uniform thickness over the whole of this length and defining an internal opening 4 which is to receive the semen and whose diameter is very substantially greater than the thickness of the cylindrical wall, for example of the order of five to ten times this thickness.

The end 3 of this tube terminates in a brim 5 which comprises a fold of the end of the main wall of this tube, this brim being folded inside the tube over a length which, in the axial direction, is for example of the order of half the inner diameter of the opening 4.

The brim 5 is shaped so that its free edge 6 comes into direct contact with the main cylindrical wall of the tube, and this brim presents over its whole length between the end 3 and its free edge 6 a continuous concavo-convex shape, that is to say without any sharp crease or corner, but on the contrary a continuous curve, both on its edge facing outwards and over all the part within the tube. The section of the brim preferably presents a semi oval shape, at least approximately, so that the profile offered by the whole brim is analogous to that of a trumpet or venturi.

In other words, this brim presents successively, in the axial direction and from the inside towards the free end 3 of the tube, first a converging part 5*a* which terminates on the inside in the free edge 6, then a diverging part 5*b* which is connected by a collar part with the corresponding end 3 of the tube 1.

Such a stock can then receive a column of animal semen 7, whose outer meniscus engages the converging part 5*a* of the brim. Thus, as mentioned above, due to the shape of this converging part, the column of semen is maintained inside the tube, even if there is a shock, whereas on the contrary when air pressure is applied to the opposite end when an insemination is to be performed, once the column of semen 7 engages within the brim 5, its total expulsion out of the tube can be favoured by the divergent part 5*b* without any of it risking being left inside.

Figure 2:
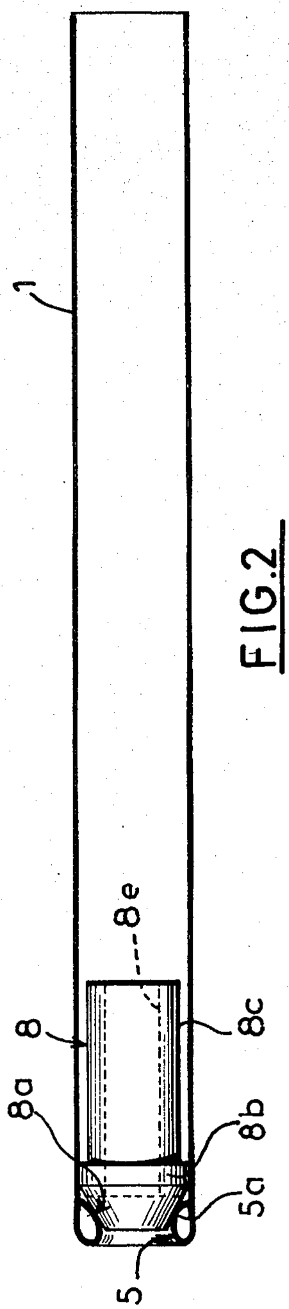
FIG. 2 shows a diametral sectional view to an enlarged scale of a semen stock in an additional embodiment of the invention, with its piston shown engaging the brim of the tube.

In the embodiment of FIG. 2, inside the tube there is positioned a member forming a piston 8 which comprises, at its end facing the brim 5 of the tube a projecting head 8*a* having a truncated cone shape converging towards the brim 5 and extended back by a short cylindrical section 8*b* connecting with the body of the piston 8*c* by an annular shoulder 8*d*. The profile of the front of the head mates approximately with the inner converging part 5*a* of the brim, and there is practically no free space left between the head 8*a* of the piston and this brim 5 when the piston approaches the brim.

This head 8*a*, and particularly its cylindrical section 8*b*, present an outer diameter matching, without play, the inner diameter of the tube 1 so as to slide in sealing engagement within the tube. This body 8*c* is of cylindrical shape and its outer diameter is less than the inner diameter of the tube 1 at its back end is formed a blind axial hole 8*e*.

Figure 3:
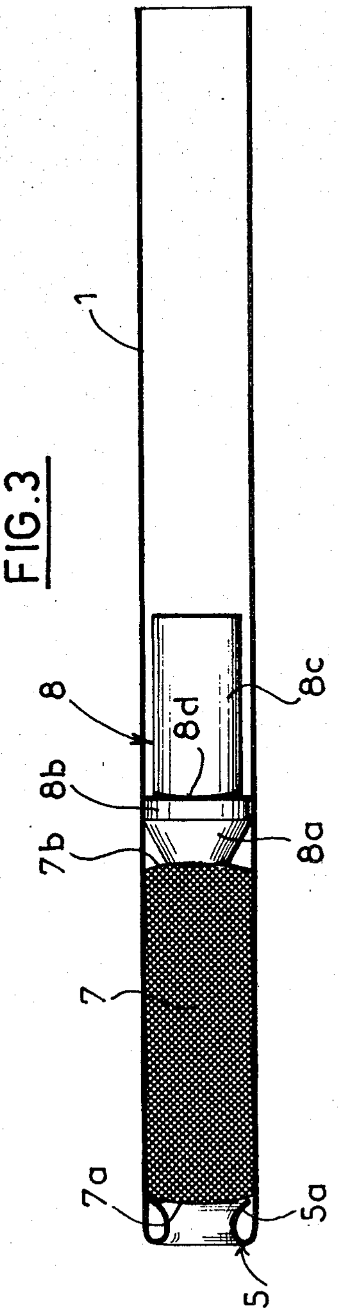
FIG. 3 shows the same stock, after a column of semen has been sucked into the tube.

When the tube, with its piston engaging the brim 5 is presented to a volume of animal semen, and the piston 8 is displaced backwards towards the opposite end of the tube, a column of semen 7 fills the tube, with its two end meniscuses 7*a* and 7*b* engaging one the inner converging part 5*a* of the brim and the other the head 8*a* of the piston, as shown in FIG. 3.

Thus, due to this double engagement, the column of semen is perfectly retained inside the tube, in spite of any shocks to which the tube may be subjected.

Moreover, during intentional expulsion of the semen for insemination, when the piston pushes the column of semen 7 out, the whole volume of the semen is evacuated with no waste, given that the truncated cone head engages very precisely against the brim 5 in the position shown in FIG. 2.

We claim:

1. A single-shot semen stock for artificially inseminating poultry, comprising a flexible tube having a hollow cylindrical portion of diameter small enough to contain semen by capillarity and presenting an inner diameter substantially greater than its wall thickness, and a reentrant brim at an open end of said tube and integral with said cylindrical portion, wherein said brim presents a free edge in direct contact with the inside of said cylindrical portion of the tube.

2. A semen stock as claimed in claim 1, characterised in that said brim has axially successive inner and outer portions which respectively converge and diverge towards the adjacent end of the tube.

3. A semen stock as claimed in claim 1 characterised in that said brim presents, over the whole of its length between its free edge and the adjacent end of said cylindrical portion, a continuous concavo-convex shape.

4. A semen stock as claimed in claim 3, wherein the section of said brim presents a substantially semioval profile.

5. A semen stock as claimed in claim 1 characterised in that it includes a piston disposed within said cylindrical portion of the tube in sliding and sealing relation therewith.

6. A semen stock as claimed in claim 5, characterised in that said brim presents an inner portion converging towards the adjacent end of the tube and said piston presents an end portion for engaging within said inner portion of the brim, said end portion of the piston also presenting a shape converging towards the adjacent end of the tube.

7. A semen stock as claimed in claim 6 characterised in that said end portion of the piston is of truncated cone shape.

8. A semen stock as claimed in claim 6 characterised in that said piston comprises a short cylindrical portion in sealing engagement with said cylindrical portion of the tube, and a further cylindrical portion projecting away from said brim and of smaller diameter than the inner diameter of said cylindrical portion of the tube.

9. A semen stock as claimed in claim 5 characterised in that said piston defines a blind hole at its end further from said brim.

10. A semen stock for artificially inseminating poultry, comprising a single shot dose of semen, an open ended flexible tube having a hollow cylindrical portion in which said dose is maintained by capillarity and presenting an inner diameter substantially greater than its wall thickness, and a reentrant brim at an open end of and integral with said cylindrical portion, whereby said brim presents in axial succession an inner free edge in direct contact with the inside of said cylindrical portion of the tube, and first and second portions which respectively converge and diverge in a continuous concavo-convex shape.

11. A semen stock as claimed in claim 10 characterised in that it includes a piston disposed within said cylindrical portion of the tube in sliding and sealing relation therewith, said dose of semen being retained between said brim and said piston.

* * * * *